US006355248B1

(12) United States Patent
Michaels et al.

(10) Patent No.: US 6,355,248 B1
(45) Date of Patent: Mar. 12, 2002

(54) METHOD OF MODULATING AN IMMUNE RESPONSE IN AN INFECTED MAMMAL BY TRANSMUCOSAL ADMINISTRATION OF MODULATING AGENT

(75) Inventors: Frank Michaels, Havertown; Timothy Block, Doylestown, both of PA (US)

(73) Assignee: Thomas Jefferson University, Philadelphia, PA (US)

(*) Notice: Subject to any disclaimer, the term of this patent is extended or adjusted under 35 U.S.C. 154(b) by 0 days.

(21) Appl. No.: 09/334,819

(22) Filed: Jun. 17, 1999

Related U.S. Application Data

(63) Continuation of application No. PCT/US98/04116, filed on Jan. 2, 1998.
(60) Provisional application No. 60/034,596, filed on Jan. 2, 1997.

(51) Int. Cl.[7] ........................ A61K 39/29; A61K 39/385
(52) U.S. Cl. .................. 424/189.1; 424/193.1; 424/227.1; 514/49
(58) Field of Search ............................ 424/189.1, 193.1; 514/227.1, 49

(56) References Cited

U.S. PATENT DOCUMENTS 5,980,898 A * 11/1999 Glenn ..................... 424/184.1

OTHER PUBLICATIONS

Chang, CN, et al., Biochemical pharmacology of (+)– and (−)-2′, 3′–dideoxy-3-′thiacytidine as antihepatitis B virus agents. J. Biol. Chem. 267(31):22414–22420, 1992.*
van Leeuwen, R, et al. The safety and pharmacokinetics of a reverse transcriptase inhibitor, 3TC, in patients with HIV infection: a Phase I study, AIDS 6:1471–1475. (1992).*
Araki et al., 1989, Proc. Natl. Acad. Sci. USA 86:207–211.
Bergerot et al., 1994, J. Autoimmun. 7:655–663.
Bolivar et al., 1997, Gene 2:95.
Broach, 1983, Meth. Enzymol. 101:307.
Broach et al., 1978, Gene 8:121.
Challoner et al., 1995, Proc. Natl. Acad. Sci. USA 92:7440–7444.
Clarke et al., 1983, Meth. Enzymol. 101:300–307.
Cohen et al., 1972, proc. Natl. Acad. Sci. USA 69:2110–2114.
Crossway et al., 1986, Mol. Gen Genet 202:179–185.
Deikman et al., 1988, EMBO J. 7:3315–3320.
Depicker et al., 1982, J. Mol. Appl. Gene. 1:561.
Deshayes et al., 1985, EMBO J. 4:2731–2737.
Farza et al., 1988, J. Virol. 62:4144–4152.
Gelfand, 1974, Postgrad. Med. 55:263–264.
Gerlich, 1993, In: *Viral Hepatitis: Scientific Basis and Clinical Management*, Zukerman et al., eds., Churchill Livingstone, Edinburgh, UK, pp 83–114.
Goeddel et al., 1980, Nucl. Acids Res. 8:4057.
Good et al., 1960, Am. J. Med. 29:804–810.
Griffiths et al., 1997, Meth. Molec. Biol. 75:427–440.
Hancock et al., 1993, Transplantation 55:1112–1118.
Hess et al., 1968, J. Adv. Enzyme Req. 7:149.
Hitzeman et al., 1980, J. Biol. Chem. 255:12073–12080.
Holland et al., 1978, Biochemistry 17:4900–4907.
Holland et al., 1981, J. Biol. Chem. 256:1385–1395.
Hsiao et al., 1979, Proc. Natl. Acad. Sci. USA 76:3829–3833.
Kumagai et al., 1993, Proc. Natl. Acad. Sci. USA 90:427–430.
Lee et al., 1989, Cancer Res. 49:403–409.
Lincoln et al., 1988, Mol. Gen. Genet. 212:71–75.
Matsunaga et al., 1992, J. Gen. Virol. 73:763–766.
Maxam et al., 1980, Methods in Enzymology 65:499–560.
Roingeard et al., 1990, Hepatology 11:277–285.
Shaw et al., 1983, Gene 23:315.
Shimatiake et al., 1981, Nature 292:128.
Soldan et al., 1997, Nature Med. 3:1394–1397.
Solignac et al., Mol. Gen. Genet. 197:183–188 (1984).
Stinchcomb et al., 1979, Nature 282:39.
Takamatsu et al., EMBO J. 6:307–311 (1987).
Trentham et al., 1993, Science:1727–1730.
Truve et al., 1993, Bio/Technology 11:1048.
Tschumper et al., 1980, Gene 10:157.
Uy et al., 1986, Virology 155:89–96.
Valenzuela et al., 1982, Nature 298:347–350.
Van Solingen et al., 1977, J. Bacteriol. 130:946.
Ward et al., 1988, EMBO J. 7:1583–1587.
Weiner et al., 1993, Science 259:1321–1324.

* cited by examiner

Primary Examiner—David Saunders
Assistant Examiner—Mary Beth Tung
(74) Attorney, Agent, or Firm—Drinker Biddle & Reath LLP

(57) ABSTRACT

Methods and compositions for modulating an immune response in a mammal infected with a bacterium, a virus, or a parasite are provided. The methods and compositions are useful in mammals experiencing an acute infection and in mammals experiencing a chronic infection. The methods and compositions may be used in conjunction with a known treatment for infection of a mammal by an infectious agent. Methods and compositions for transmucosal delivery of a molecule comprising an epitope located in close proximity to the immune response are provided.

27 Claims, 5 Drawing Sheets

Adoptive transfer recipient transgenic (HBV+) and non-transgenic (HBV-) littermate SCID mice.
Liver section (5 μm) Hematoxylin & Eosin stain 21 days post reconstitution.

Mag: 400X

Adoptive transfer recipient transgenic (HBV+) and non-transgenic (HBV-) littermate SCID mice.
Liver section (5 μm) Hematoxylin & Eosin stain 21 days post reconstitution.
Mag: 200X

METHOD OF MODULATING AN IMMUNE RESPONSE IN AN INFECTED MAMMAL BY TRANSMUCOSAL ADMINISTRATION OF MODULATING AGENT

This application is a continuation of copending International application PCT/US98/04116 filed on Jan. 2, 1998 and published in English under PCT Article 21(2) on Jul. 9, 1998 publication no. WO 98/29121), which claims the benefit of U.S. provisional application Ser. No. 60/034,596, filed Jan. 2, 1997.

FIELD OF THE INVENTION

The field of the invention is modulation of the immune response of a mammal infected with an infectious agent.

BACKGROUND OF THE INVENTION

Numerous bacterial, viral, and parasitic infections of mammals have two phases of infection: an acute phase during the early stages of the infection, sometimes followed by a prolonged chronic phase having a finite or indefinite duration. The ability of an infectious agent to establish a chronic infection in a mammalian host depends to a significant extent on the capacity of the host immune response to eliminate the infecting organism from the host in the early stages of the infection. The specific immune mechanisms responsible for eliminating the infectious agent from the host differ depending on the infectious agent. In the case of viral and some parasitic infections, the infectious agent-eliminating activity of cytotoxic T lymphocytes is believed to comprise a pivotal component of the host immune response for mediating the elimination of these agents from the host.

The components of a mammalian immune system to which mammalian immune response activities can be attributed include, but are not limited to, antibody molecules, complement molecules, B lymphocytes, T lymphocytes, cytotoxic T lymphocytes, helper T cells, suppressor T cells, immunosuppressive lymphocytes, cytokine-secreting lymphocytes, other non-cytotoxic lymphocytes, macrophages, neutrophils, mast cells, basophils, eosinophils, monocytes, and the like. Induction or replication of the host immune activities leading to complete elimination of an infectious agent from a mammalian host is the paradigm for a clinical treatment for infection by a infectious agent.

In the course of infections with bacteria and some parasites, elimination from a host of an infectious agent causing an acute infection has traditionally been accomplished using antibiotics which serve as relatively selective poisons for the infectious agent. Antibiotic treatment has been less successful in the case of chronic bacterial infection. More recently, clinical efforts have focused on modulating the host immune system in an attempt to eliminate infectious agents causing chronic infections in cases wherein indolence of the host immune system contributes to persistence of the infectious agent. Specific immune modulation using substances such as interferons alpha, beta, and gamma has been attempted, and in a minority of cases beneficial results have been observed.

When an infection becomes chronic, the infection may be controlled by a persistent host immune reaction to the infectious agent. Certain herpes viruses, for example, remain latent only in the context of host immune competence. Immunosuppressive therapy used, for example, in organ transplant recipients permits latent herpes virus to become reactivated. Thus, loss of immune competence in response to steroid and cyclosporin A administration to a human patient having a latent HHV-6 infection permits recrudescence of HHV-6. The result of HHV-6 reactivation includes viral pneumonia and bone marrow suppression. In addition, the high incidence of non-Hodgkins B cell lymphomas among humans infected with the AIDS virus (HIV-1) demonstrates that pathogenicity attributable to chronic Epstein-Barr virus infections becomes active as T cell competence is lost. Thus, reactivation of pathogenicity attributable to an otherwise non-pathogenic chronic infection which is effected by suppression of the host's immune competence may have deleterious effects on the host.

Several microbial infectious agents cause disease in a mammalian host predominantly by eliciting a host immune response which is ineffective in eliminating the infectious agent from the host, but is effective in damaging or destroying host tissues. One such virus which functions in this manner is the AIDS virus, HIV-1. HIV-1 mediates destruction of helper T lymphocytes in HIV-1-infected humans, but the mechanism of cellular destruction has not been unequivocally defined. Although helper T cells are destroyed in culture by syncytium formation, the presence of multi-nucleated T cells in patient samples has not been reported. This suggests that in vivo syncytium formation is a rare event. It is known that patients infected with HIV-1 develop a strong cytotoxic response to the virus, and that this response persists throughout the course of the infection. It is also known that at least some of the T cell loss characteristic of AIDS is the result of the death of CD4-bearing T cells which express viral antigens within the context of MHC class I molecules. The death of these cells is mediated by the immune system in the infected individual.

HTLV-I, another human retrovirus, does not directly damage host cells. Patients chronically infected with HTLV-1 frequently exhibit a slowly developing neurological disease, namely HTLV-I associated myelopathy/tropical spastic paraparesis (HAM/TSP). HAM/TSP is clinically and histopathologically similar to the human autoimmune disease, multiple sclerosis (MS).

In humans afflicted with MS, neural elements are lost, apparently due to the immune reactivity of the patient to viral antigens in the neuropil. It has been suggested that MS has an infectious etiology. Although several viruses have been suggested to be the pathogenic trigger for the development of MS, recent experimental evidence strongly suggests that human herpesvirus 6 (HHV-6) may be the infectious agent ultimately responsible for development of MS in humans. Replicating HHV-6 has been identified in MS plaques (Challoner et al., 1995, Proc. Natl. Acad. Sci. USA 92:7440–7444). Furthermore, the majority of humans having the relapsing-remitting form of MS exhibit evidence of an immune reaction to acutely replicating HHV-6 (Soldan et al., 1997, Nature Med. 3:1394–1397). These observations suggest that MS, which has long been classified as an autoimmune disease, may result from chronic infection of a human with HHV-6. If this is true, a human afflicted with MS would benefit from suppression of the immune response to the presence of HHV-6 in the human.

Certain chronic bacterial and protozoal infections also mediate disease in a mammalian host by inducing persistent host immune reactivity coupled with ineffective elimination of the infectious agent from the host. For example, *Mycobacterium tuberculosis* is a slow growing organism which causes tissue destruction primarily via the host autoimmune response. Similarly, the protozoan *Leishmania donovani* is itself relatively non-pathogenic, but a persistent host immune reaction to infection results in severe disease. Lymphatic filariasis leads to partial occlusion of the lymph channels, but the contribution of the persistent ineffective immune reaction to the parasite is also responsible for the loss of lumen patency with the resulting disfiguring elephantiasis. Mammalian infection by *Leishmania braziliensis* frequently leads to severe mutilating facial lesions which appear years after the original facial lesion has healed. The severe lesions are caused by repeated attempts by the immune system to destroy small numbers of the parasite remaining in the host. Similarly, parasites such as *Schistosoma mansoni* cause scarring of the hepatic portal tracts by inducing a persistent immune reaction to parasites dwelling within the liver. The immune reaction does not clear the infection, circulatory difficulties result, and life threatening cirrhosis with portal hypertension may ensue.

Perhaps the most illustrative example of a class of infectious agents that are intrinsically non-pathogenic in the absence of a persistent immune response is hepatitis B virus (HBV). Most individuals who become infected with HBV exhibit few clinical symptoms and eliminate the virus from their system within several weeks following exposure. About 10% of acutely HBV-infected individuals develop chronic infection. The factors which predispose individuals to chronic infection are largely unknown. HBV is ubiquitous, and the worldwide population of chronically HBV-infected individuals has been estimated by the World Health Organization at approximately 350 million. A large percentage of patients chronically infected with HBV develop life threatening cirrhosis and primary hepatocellular carcinoma as a direct result of the daily assaults on the liver by the immune system in an attempt to clear the virus.

The mechanisms ultimately responsible for HBV-mediated cirrhosis are immunopathological. Liver injury does not result directly from infection with HBV. This statement is supported by the finding that up to 70% of the hepatocytes in the liver of chronically-infected human patients harbor virus even though clinical evidence of hepatitis may be mild (Ray, 1978, *Hepatitis B virus antigens in tissues,* University Park Press, Baltimore, pp 49–68). Furthermore, results of experiments investigating the interaction of HBV and host cells, both in vitro and in vivo, indicate that the virus has no detectable cytotoxic or cytolytic activity. HepG2 cells have been shown to express HBV after transfection with no apparent alteration in cellular function (Roingeard et al., 1990, Hepatology 11:277–285). Recent studies employing immunocompetent transgenic mice comprising the HBV genome have shown that none of the viral antigens possess direct cytotoxic potential. Although all of the principal HBV proteins were detected in liver cells, or were present in the circulation in these mice, no evidence of cytotoxicity of these cells was observed (Araki et. al., 1989, Proc. Natl. Acad. Sci. USA 86:207–211; Farza et. al., 1988, *J. Virol.* 62:4144–4152).

Acute HBV infection in humans results in a vigorous anti-virus host immune response. All of the viral proteins, including the viral surface protein (HBsAg) and the nucleocapsid (core, HBcAg), provoke the production of specific immunoglobulins. Vaccination trials have proven that antiviral antibody is critical in preventing de novo HBV infection, but that the humoral component of the immune response is of minimal utility for controlling established infection (Krugman et al., 1994, "Hepatitis B vaccine", In: *Vaccines,* Plotkin et al., eds., W. B. Saunders, Philadelphia; Gelfand, 1974, *Postgrad. Med.* 55:263–264; Good et al., 1960, *Am. J. Med.* 29:804–810). In addition, the concentration of anti-HBsAg antibodies falls to undetectable levels in the majority of chronically infected patients, further suggesting the lack of utility of these antibodies in modulating chronic HBV infection (Gerlich, 1993, In: *Viral Hepatitis: Scientific Basis and Clinical Management.* Zukerman et al., eds., Churchill Livingstone, Edinburgh, UK, pp 83–114). The role of the cellular component of immune defense is not so benign.

HBV-driven hepatocellular necrosis in chronically infected individuals is the result of immune cytotoxic T cells which react with viral antigens which are presented in conjunction with host MHC class I molecules on the surface of infected hepatocytes. Host immune control of the virus is not only ineffective, but is actually detrimental to a chronically infected host. The remissive/exacerbative nature of HBV-associated liver disease in chronically infected patients probably results from variations in host immune reactivity, rather than from variability in viral antigen expression. Such host variability has been suggested to result from changes in the concentration of MHC class I antigen expression on the surface of HBV-infected hepatocytes, and is the rational basis for the clinical use of alpha- and beta-interferons to treat chronic HBV infections.

The principles of oral tolerance therapy have been successfully applied to the treatment of a number of human autoimmune diseases. Preliminary results from Phase III trials of such therapies for treatment of multiple sclerosis and for treatment of rheumatoid arthritis have been reported (Weiner et. al., 1993, Science 259:1321–1324; Trentham et. al., 1993, Science 261:1727–1730). In additional, the efficacy of oral tolerance therapy has been demonstrated in animal models of allograft rejection and type II diabetes (Hancock et. al., 1993, Transplantation 55:1112–1118; Bergerot et al., 1994, J. Autoimmun. 7:655). Oral tolerance therapy has never been attempted for treatment of viral, bacterial, or parasitic infections because such endeavors were considered counterproductive and contraindicated in view of the clinician's primary goal of clearing the infectious agent from the patient.

The immune response of a mammalian host to infection by an infectious agent may result in elicitation of an immune response to tissue antigens normally expressed by the host. By way of example, a known reaction to infection of a human by a group B hemolytic Streptococcus species is development of rheumatic fever. One or more specific streptococcal antigens stimulate production of a component of the host immune response which recognizes not only the infecting bacterium, but also antigens expressed by normal tissues present in the heart and joints of the patient. With prolonged infection, such as that which occurs in the absence of effective antibiotic treatment of the bacterial infection, the host immune system attacks normal tissues, and heart valvular defects ensue from tissue scarring mediated by the immune response. Furthermore, the patient develops arthritis, due to the response of the same component(s) of the immune system to tissues in the joints of the patient.

A similar set of disease manifestations has been reported following *Streptococci mutans* infection of humans secondary to dental treatment. *S. mutans* is a constituent of the normal flora of the oropharynx, and is a causative agent of dental caries. The trauma associated with dental care frequently results in the mechanical transmission of the bacterium to the patient's circulation, whereby a focal infection may result. As with infection by group B hemolytic Streptococcus bacteria, one or more components of the immune system developed against the infectious agent begin destroying normal tissues, and a pathological condition results.

Parasitic diseases represent additional examples of the class of diseases which elicit a destructive autoimmune response in a mammalian host. For example, infection of a human by *Onchocera volvulus*, the causative agent of "river blindness," elicits production of antibodies which are cross-reactive with a protein normally found in the human retina. In humans infected with *Trypanosoma cruzi*, the antigen designated FI-160 elicits production of antibodies which cross-react with a protein present in the central nervous system. Thus one of the disease presentations of *T. cruzi* is an immune-mediated destruction of the neural plexus. South American Sleeping. Sickness, also designated Chagas disease, is caused by infection of a human by *T. braziliensis*, which elicits immune-mediated destruction of cardiac and neural tissues.

There is a critical need for methods and compositions which are useful for modulating the undesirable autoimmune responses exhibited by mammals infected with viral, bacterial, and parasitic agents. The current invention is useful for preventing the life-long disabilities which result from these infections.

BRIEF SUMMARY OF THE INVENTION

The invention relates to a method of modulating an immune response in a mammal infected with an infectious agent, the method comprising transmucosally administering a composition to the mammal. The composition comprises an epitope which is located in close proximity to the immune response in the mammal. Following administration of the composition to the mammal, the immune response is modulated. The mammal may be chronically infected with the infectious agent.

In one embodiment of the method of the invention, the infectious agent comprises an antigen which comprises the epitope. In this case, the composition may comprise the antigen.

In another embodiment of the method of the invention, the mammal comprises an antigen which comprises the epitope. In this case, the antigen may be one which reacts with a component of the immune system of the mammal only when the mammal is infected with the infectious agent. By way of example, the component may be selected from the group consisting of an antibody molecule, a complement molecule, a B lymphocyte, a T lymphocyte, a helper T lymphocyte, a suppressor T lymphocyte, a cytotoxic T lymphocyte, an immunosuppressive lymphocyte, a cytokine-secreting lymphocyte, a non-cytotoxic lymphocyte, a macrophage, a neutrophil, a mast cell, a basophil, an eosinophil, and a monocyte.

In another aspect of the method of the invention, the mammal is a human.

In yet another aspect of the method of the invention, the composition further comprises a second molecule selected from the group consisting of an antibiotic, an antiviral compound, an antiparasitic compound, an anti-inflammatory compound, an immunosuppressant, and a synergist. By way of example, the second molecule may be selected from the group consisting of lamivudine, a bacterial lipopolysaccharide, an immunoregulatory lipoprotein, a peptide covalently linked to tripalmitoyl-S-glycarylcysteinyl-seryl-serine, a steroid, cyclosporin A, AZT, ddC, ddI, and 3TC.

In still another aspect of the method of the invention, the infectious agent is selected from the group consisting of a bacterium, a virus, and a parasite. By way of example, the infectious agent may be selected from the group consisting of hepatitis B virus, hepatitis C virus, parvovirus B19, Borna disease virus, HIV, HTLV-1, *Mycobacterium tuberculosis*, a group B hemolytic *Streptococcus bacterium*, *S. mutans*, *Trypanosoma cruzi*, *Leishmania donovani*, *Onchocerca volvulus*, *T. braziliensis*, and *S. mansoni*.

In another aspect of the method of the invention, the immune response is selected from the group consisting of an autoimmune reaction, a humoral immune response, and a cellular immune response. By way of example, the autoimmune reaction may selected from the group consisting of a humoral immune response comprising production of an antibody which cross-reacts with a tissue antigen of the mammal, a humoral immune response comprising production of an immunosuppressive factor, a cellular immune response comprising production of a cytotoxic cell which specifically induces cell death in a tissue of the mammal, and a cellular immune response comprising production of a lymphocyte which secretes an immunosuppressive factor.

In still another aspect of the method of the invention, transmucosal administration of the composition is accomplished by a route of administration selected from the group consisting of oral, enteral, intranasal, pulmonary, and colonic.

In other embodiment, the method of the invention further comprises administering to the mammal a composition comprising a second molecule selected from the group consisting of an antibiotic, an antiviral compound, an antiparasitic compound, an anti-inflammatory compound, an immunosuppressant, and a synergist. By way of example, the second molecule may be selected from the group consisting of lamivudine, a bacterial lipopolysaccharide, an immunoregulatory lipoprotein, a peptide covalently linked to tripalmitoyl-S-glycarylcysteinyl-seryl-serine, a steroid, cyclosporin A, AZT, ddC, ddI, and 3TC.

The invention also relates to a composition for modulating an immune response in a mammal infected with an infectious agent, the composition comprising an epitope which is located in close proximity to the immune response in the mammal.

DETAILED DESCRIPTION

Figure 1:
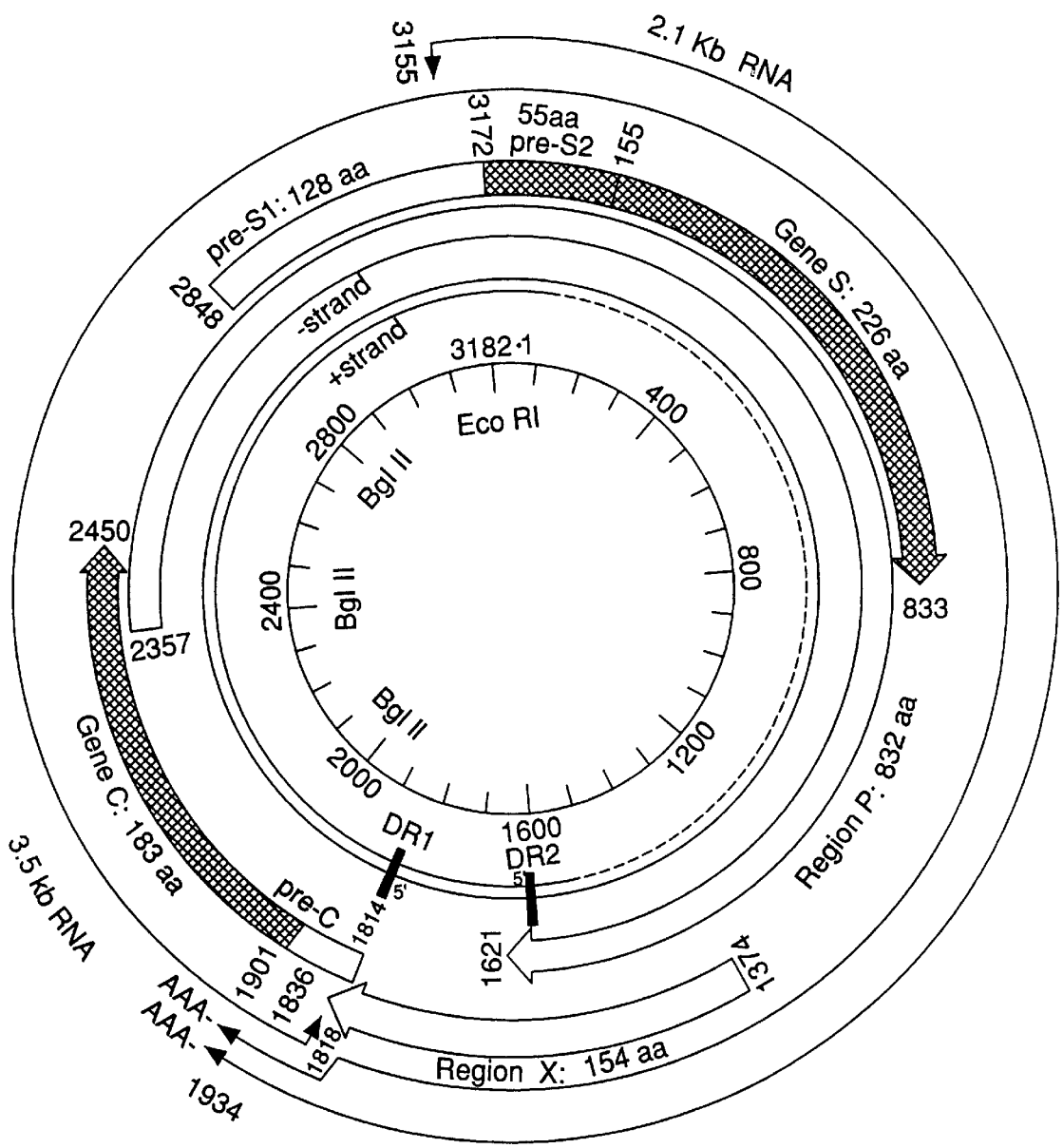
FIG. 1 is a representation of the genome of the hepatitis B virus.

The present invention provides a method of modulating an immune response of a mammal, such as a human, infected with an infectious agent. The method is useful to treat mammals which are acutely infected with an infectious agent and mammals which are chronically infected with an infectious agent. The method comprises transmucosally administering to the mammal a composition comprising an epitope located in close proximity to the immune response.

As used herein, "modulating an immune response of a mammal" means increasing or decreasing either the amount of a component of the immune system or the activity by which a component of the immune system is characterized. By way of example, modulating an immune response of a human includes increasing the number of suppressor T lymphocytes present in the human, increasing secretion of immunosuppressive factors by a suppressor T lymphocyte in the human, decreasing the number of cytotoxic T lymphocytes present in the human, decreasing the cytotoxic activity of a cytotoxic T lymphocyte in the human, decreasing the amount of an antibody in the human, decreasing the amount of a complement protein in the human, decreasing the ability of a complement protein to interact with a cell in the human, and the like.

As used herein, an "epitope" means a molecule or a portion of a molecule which interacts or is capable of interacting with an immunoglobulin molecule produced by the immune system of a mammal such as a human. An antigen is a well known example of an epitope which is capable of interacting with an antibody. It is understood that a single molecule may comprise numerous epitopes, and that an epitope may comprise a portion of each of more than one molecule.

According to the method of the invention, "an epitope located in close proximity to the immune response" means an epitope present on the surface of at least one cell of a tissue located at a site of undesirable immune reactivity, wherein the reactivity is induced or exacerbated by the presence in the mammal of the infectious agent, or an epitope which is cross-reactive with such an epitope. By way of example, the presence of the hepatitis B virus (HBV) induces the human body to produce cytotoxic T lymphocytes which attack hepatic cells that display a viral protein comprising a particular epitope on their surface. In this case, both production of these T lymphocytes and the cytotoxic activity of these T lymphocytes toward hepatic cells are undesirable immune reactivities. By transmucosally administering to an HBV-infected human a composition comprising the same or a similar epitope, immunosuppressive lymphocytes such as suppressor T lymphocytes are produced by the body. These lymphocytes are capable of migrating to the hepatic tissue which displays the epitope and of suppressing the cytotoxic activity of T lymphocytes produced in response to the presence in the human of HBV, thereby modulating the undesirable immune reactivity.

A first epitope is "cross-reactive" with a second epitope if the first epitope interacts or is capable of interacting with an immunoglobulin molecule produced by the immune system of a mammal such as a human and the second epitope interacts or is capable of interacting with the same immunoglobulin molecule.

The immune response modulated by the method may be an autoimmune reaction, a humoral immune response to infection by the infectious agent, a humoral immune response to infection by the infectious agent wherein the humoral response comprises production of an antibody which cross-reacts with a tissue antigen of the mammal, a cellular immune response to infection by the infectious agent, a cellular immune response to infection by the infectious agent wherein the cellular response comprises production of a cytotoxic cell which specifically induces cell death in a tissue of the mammal, and the like.

Humoral immune responses which can be modulated using the method of the invention include, but are not limited to, production of an antibody molecule by the mammal, production of a cytokine by the mammal, production of a complement protein molecule by the mammal, and the like. Cellular immune responses which can be modulated using the method of the invention include, but are not limited to, production of an antibody-producing cell, production of a cytotoxic T lymphocyte, production of a suppressor T cell, production of a T helper cell, production of an immune memory cell, and the like.

The epitope of the molecule administered according to the method of the invention may be an epitope located on an antigen of the infectious agent, or an epitope located on a tissue antigen of the mammal. When the epitope is an epitope located on a tissue antigen of the mammal, the tissue antigen may be a tissue antigen which does not normally react with a component of the immune system of the mammal, but which reacts with the component when the mammal is infected by the infectious agent.

The present invention also provides an improved method of treating a chronic infection of a mammal by an infectious agent, the improved method comprising any known method of treating the chronic infection performed in conjunction with administration on to the mammal of a composition comprising an epitope located in close proximity to a site of undesirable chronic immune reactivity. The known method may be performed before, after, or simultaneously with administration of the epitope. For example, the known method may be performed within one month of administration of the epitope, and is preferably performed within one week of administration of the epitope. Such known methods include administration of such compounds as lamivudine, a bacterial lipopolysaccharide, an immunoregulatory lipoprotein, a peptide covalently linked to tripalmitoyl-S-glycarylcysteinyl-seryl-serine, a steroid, cyclosporin A, AZT, ddC, ddI, 3TC, and the like.

The Method of the Invention

The method of the invention comprises modulating an immune response of a mammal by transmucosally administering to the mammal a composition comprising an epitope which is located in close proximity to the immune response. One embodiment of the method of the invention, comprising orally administering the composition, is herein alternately designated "oral antigen tolerization therapy" or "induction of oral tolerance."

Recent studies suggest that the pathological consequences of chronic infections of mammals by various infectious agents may be the result of a low, persistent immune response elicited by the presence of the infectious agent in the mammal. It has been discovered that symptoms exhibited by mammals chronically infected with an infectious agent may be improved by modulation of the persistent agent-induced immune response in the mammal. Modulation of the immune response will not have deleterious consequences in a mammal infected with an infectious agent which is non-pathogenic. Furthermore, where the infectious agent exhibits limited pathogenicity but the immune response to the infectious agent causes more significant pathogenicity, it is desirable to ablate the pathogenicity caused by the immune response by modulating that immune response, even though the pathogenicity attributable to the infectious agent remains.

By way of example, it has been reported that essentially 100% of the liver cells of a chronically HBV-infected human contain replication competent virus. Thus, the immune response to the virus apparently does not control the spread of HBV in the patient. Furthermore, HBV is not directly pathogenic to liver cells. Instead, the immune response of the patient to the presence of HBV causes damage to the liver cells. Therefore, HBV infection is an example of infection of a mammalian cell with an infectious agent wherein the infectious agent exhibits limited pathogenicity but the immune response to the infectious agent causes more significant pathogenicity.

Similarly, HIV-1 does not directly damage host T lymphocytes in a human infected with HIV-1. Instead, the T lymphocytes are killed by the immune system through the action of cytotoxic lymphocytes which are activated in response to HIV-1 infection. Other chronic infectious agents which do not themselves damage the tissue of a human host, but which result in host-mediated damage to itself include HTLV-I, *Mycobacterium tuberculosis, Leishmania donovani,* group B hemolytic Streptococcus species, *Trypanosoma cruzi, Onchocerca volvulus, T. braziliensis,* and *S. mutans.*

Thus, it is highly desirable to modulate the immune response of a mammal which is elicited in response to certain chronic infections. In particular, it is highly desirable to modulate the immune response of a human which is elicited in response to certain infectious agents including, but not limited to, those described herein.

The method of the invention comprises transmucosal administration of one or more therapeutic epitopes to a mammal. Transmucosal administration of an epitope may be accomplished by delivering the epitope to a mammal orally, enterally, intranasally, by a pulmonary route, colonically, or by any other known transmucosal delivery route. Colonic administration, as used herein, means administration to any portion of the large intestine, such as by rectal administration. Oral administration which does not bypass the stomach is preferred. For inhalation methods, treatment is preferably through the bronchial and pulmonary mucosa.

The method of the present invention includes both prophylactic treatment measures which prevent damage caused by the immune response elicited in response to a chronic infection and therapeutic treatment measures which ameliorate clinical symptoms resulting from damage caused by this immune response. Any clinically or statistically significant attenuation of even one symptom associated with a an undesirable immune response following treatment in accordance with the method of the present invention is included within the scope of the invention. By way of example, increased liver size, the presence of tumors and ascites, elevated serum levels of alpha-feto-protein, fever, and pain, are associated with hepatocellular carcinoma associated with chronic HBV infection in a human. Amelioration or elimination of one or more these symptoms using the methods described herein is within the scope of the present invention.

Prophylactic treatment according to the method of the invention includes, but is no limited to, transmucosal administration of an epitope of an infectious agent to a mammal prior to infection of the mammal with the infectious agent, transmucosal administration of an epitope of an infectious agent to the mammal following infection of the mammal with the infectious agent but prior to exhibition of an undesirable immune response of the mammal elicited by such infection, transmucosal administration to the mammal of an epitope displayed by a tissue of the mammal prior to infection of the mammal with the infectious agent, transmucosal administration to the mammal of an epitope displayed by a tissue of the mammal following infection of the mammal with the infectious agent but prior to exhibition of an undesirable immune response of the mammal elicited by such infection, and the like.

Therapeutic treatment according to the method of the invention includes, but is not limited to, transmucosal administration of either an epitope of an infectious agent or an epitope displayed by a tissue of the mammal following infection of the mammal with the infectious agent and exhibition by the mammal of an undesirable immune response elicited by such infection.

It is contemplated that the invention is operable when used in conjunction with traditional therapies aimed at suppressing replication of an infectious agent and reinfection of cells or tissues of the host by that agent. By way of example, chronic HBV infection may be treated by simultaneously using the method described herein and administering lamivudine to a human patient.

In accordance with the method of the present invention, an epitope is administered transmucosally to a mammal which is chronically infected with an infectious agent and which exhibits a symptom of an autoimmune response, thereby inducing antigenic tolerance of the immune system of the mammal for the epitope and modulating the immune response elicited by the mammal in response to the presence of the agent.

The term "antigenic tolerance" as used herein refers to the induction of immune hyporesponsiveness following transmucosal administration of an epitope, and should not be confused with the use of the term "systemic tolerance" which refers to a circulatory immune system phenomenon. "Systemic tolerance" may be differentiated from antigenic tolerance in that the former term is applied to the functional silencing, or deletion of clones of immune cells which develop in the thymus of a mammal and which recognize normal host tissue antigens. "Antigenic tolerance" specifically refers to the induction of hyporesponsiveness to a specific epitope following the transmucosal delivery of the epitope.

The Epitope Administered in the Method of the Invention

Epitopes which may be administered to a mammalian host according to the method of the invention include, but are not limited to, an epitope of an antigen derived from the infectious agent, an epitope of an antigen which is displayed by a tissue in the mammal and which cross-reacts with a component of the host immune response, such as an antibody or a cytotoxic T lymphocyte, which is activated in response to the presence of the infectious agent, a molecule which comprises an epitope recognized by a component of the host immune response which is activated in response to the presence of the infectious agent, a molecule which comprises an epitope located in close proximity in vivo to an epitope which is displayed by a tissue in the mammal and which cross-reacts with a component of the host immune response which is activated in response to the presence of the infectious agent, and a molecule which comprises an epitope recognized by a component of the host immune response which is activated in response to the presence of the infectious agent.

Numerous methods of isolating and preparing epitopes have been described in the literature. Methods of identifying epitopes of an antigen and methods of preparing molecules comprising an identified epitope of an antigen are known in the art. The epitope which is useful in the method of the invention includes any epitope which, when transmucosally administered to a mammal, induces immune tolerance toward the epitope in the mammal. It is contemplated that any epitope of any infectious agent which induces an undesirable immune response in a mammal infected with the agent is useful in the method of the invention. It is furthermore contemplated that any epitope which is normally displayed by a tissue of such an infected mammal and which is either identical to or located in close proximity to an epitope which cross-reacts with a component of the host immune response which is activated in response to the presence of the infectious agent is useful in the method of the invention.

A first epitope is "located in close proximity to a second epitope" in a mammal if the first epitope and the second epitope are displayed by the same tissue, the first epitope is displayed by a first tissue which contacts a second tissue which displays the second epitope, or the first epitope is displayed by a first tissue in fluid communication with a second tissue which displays the second epitope. The ability to modulate an immune response elicited in response to the presence in a mammal of a first epitope by administering to the mammal a composition comprising a second epitope, wherein the first and second epitopes are located in close proximity to one another is designnated "bystander suppression."

A first epitope is "located in close proximity to an immune response" if the immune response is elicited in response to the presence in a mammal of the first epitope, the immune response is elicited in response to the presence in the mammal of a second epitope located in close proximity to the first epitope, or if the presence in the mammal of a second epitope elicits an immune response which cross-reacts with the first epitope.

An epitope is "displayed by" a tissue, as used herein, when the epitope is associated with a cell of the tissue and is accessible to a component of the immune system of the mammal which comprises the tissue. By way of example, a cell-surface protein of an epithelial cell lining an artery of a mammal is accessible to an antibody in the bloodstream of the mammal. Thus, an epitope of such a cell-surface protein is displayed by mammalian arterial epithelial tissue. An epitope is displayed by a tissue of a mammal if the epitope is normally expressed by the tissue, or if the epitope is expressed by the tissue following infection of the mammal by an infectious agent.

Bystander suppression is the result of the ability of transmucosally induced tolerant immune cells to migrate to sites of active inflammation and modulate immune reactions by secreting immunosuppressive factors such as transforming growth factor beta (TGF-$\beta$) and interleukin-10 (IL-10). For example, mammals which have been immunized with the central nervous system protein, myelin basic protein (MBP), develop a disease which is similar to multiple sclerosis in humans. If a mammal is fed MBP, the disease state can be prevented, attenuated, or completely abrogated by induction of oral tolerance toward MBP. The same disease can be likewise prevented, attenuated, or completely abrogated if animals are fed phospholipid protein, a protein which is located in close proximity to MBP in the mammalian brain. Thus, it is not necessary to identify and administer to the host the specific host epitope(s) which is recognized by a component of the host immune system which is activated in response to the presence of an infectious agent. Instead, it is sufficient to administer to the host another epitope which is normally located in close proximity to the anatomical site of the autoimmune reaction.

Thus, by way of example, an epitope may be administered to a human patient according to the method of the invention for treatment of rheumatic fever which develops in response to infection of a patient with a group B Streptococcus bacterium. Such a patient develops antibodies and reactive T cells to bacterial antigens which cross-react with a normal tissue antigen present in the synovium of the joints of the patient. If the bacterial epitope is orally administered to the patient, the patient will develop epitope-specific immune hyporesponsiveness, and destruction of tissues in the patient's joints will be suppressed. Similarly, if the tissue antigen is orally administered to the patient, the inflammatory reaction in the patient will be abrogated or significantly attenuated. In addition, the method of the invention may be practiced by administering to the patient an epitope which is normally expressed in close proximity to the tissue antigen or one which is displayed by a tissue in close proximity to the tissue antigen following infection of the patient by the bacterium. Thus, by way of example, an epitope which is normally expressed in the synovium of the joints of the patient and which is different from the tissue antigen may be administered to the patient according to the method of the invention to alleviate arthritis caused by the autoimmune response elicited in response to the presence of the bacterium.

Examples of epitopes which may be administered to a human chronically infected with HBV include, but are not limited to, an epitope of the HBV viral coat protein designated HBsAg, an epitope of the HBV core protein, or an epitope of the protein encoded by the X gene of HBV.

Infectious agents which elicit host immune responses against which the methods of the present invention are effective include, but are not limited to viral, bacterial, and parasitic infectious agents such as HBV, hepatitis C virus, parvovirus B19, Borna disease virus, HIV, HTLV-1, *Mycobacterium tuberculosis,* a group B hemolytic Streptococcus bacterium, *S. mutans, Trypanosoma cruzi, Leishmania donovani, Onchocerca volvulus, T. braziziensis,* and *S. mansoni.*

Epitopes useful in the method of the invention include epitopes which possess the ability to elicit production of immune-suppressing cells following transmucosal administration of the epitope. Such immune-suppressing cells are characterized by the fact that they secrete immunosuppressive factors such as TGF-β and IL-10 and that they have the ability to migrate to anatomical sites of persistent immune reactivity. Thus, symptoms of autoimmune reactions elicited in response to the presence in a host mammal of an infectious agent may be relieved by administering to the mammal an epitope which induces immune-suppressive cells and which is not expressed by the agent. Such epitopes may be expected to have broad applicability to modulate autoimmunue responses elicited by a variety of infectious agents.
Methods of Making the Epitope Administered in the Method of the Invention Epitopes useful in the method the present invention may be isolated from natural sources using known methods or, alternately, may be prepared recombinantly. Techniques which are used to transform cells, construct vectors, extract messenger RNA, prepare cDNA libraries, and the like are widely practiced in the art, and practitioners are familiar with standard resource materials which describe specific conditions and procedures (see, e.g. Sambrook et al., 1989, *Molecular Cloning: A Laboratory Manual,* Cold Spring Harbor Laboratory, New York; Ausubel et al., 1993, *Current Protocols in Molecular Biology* Green & Wiley, New York).

Known prokaryotic expression systems may be used to produce epitopes useful in the method of the present invention. Plasmid vectors which contain replication sites and control sequences derived from a species compatible with the host are used. In one such prokaryotic expression system, for example, *E. coli* is transfrrned using a derivative of pBR322, a plasmid derived from an *E. coli* species by Bolivar et al. (1977, Gene 2:95). pBR322 contains genes encoding proteins which confer ampicillin and tetracycline resistance and thus provide markers which can be either retained or destroyed in constructing the desired vector.

Prokaryotic control sequences useful to produce the epitope include, but are not limited to, promoters for transcription initiation such as the beta-lactamase (penicillinase) promoter system, the lactose (lac) promoter systems, the tryptophan (trp) promoter system, and the lambda derived $P_L$ promoter system, operator sequences, and ribosome binding site sequences such as the N-gene ribosome binding site (Chang et al., 1977, *Nature* 198:1056; Goeddel, et al., 1980, *Nucl. Acids Res* 8:4057; Shimatoake et al., 1981, *Nature* 292:128).

Eukaryotic organisms, such as yeast may also be used to produce the epitope used in the method of the invention, using known methods for expressing an exogenous protein in, for example, yeast. Laboratory strains of *Saccharomyces cerevisiae,* Baker's yeast, may be used, although a number of other strains are commonly available.

Vectors suitable for yeast expression include the two micron origin of replication, as well as other vectors described in the art (see, e.g., Broach, 1983, *Meth. Enzymol.* 101:307; Steinchcomb et al., 1979, *Nature* 282:39; Tschempe et al., 1980, *Gene* 10:157; Clark et al., 1983, *Meth. Enzymol.* 101:300). Control sequences for expression of genes in yeast vectors include promoters for the synthesis of glycolytic enzymes (Hess et al., 1968, *J. Adv. Enzyme Req.* 7:149; Holland et al., 1978, *Biochemistry* 17:4900). Additional yeast promoters known in the art include the 3-phosphoglycerate kinase promoter and other glycolytic enzyme promoters such as glyceraldehyde-3-phosphate dehydrogenase, hexokinase, pyruvate decarboxylase promoter, phosphoglycerate mutase, pyruvate kinase, triose phosphate isomerase, phosphoglucose isomerase, and glucokinase promoters (Hitzeman et al., 1980, *J. Biol. Chem* 255: 2073). Other promoters, which have the additional advantage of permitting transcription to be controlled by manipulating growth conditions include the promoter regions governing expression of alcohol dehydrogenase 2, isocytochrome C, acid phosphatase, degradative enzymes associated with nitrogen metabolism, and enzymes responsible for maltose and galactose utilization (Holland, supra). It is also believed that terminator sequences are desirable at the 3' end of the coding sequences in the constructs which may be used to generate the epitopes described herein. Such terminators are found in the 3' untranslated region following the coding sequences in yeast-derived genes.

Other useful vectors include those which contain control sequences derived from the enolase-gene-containing plasmid peno46 or the LEU2 gene obtained from YEp13 (Holland et al., 1981, *J. Biol Chem* 256:1385; Broach et al., 1978, *Gene* 8:121). Any vector containing a yeast compatible promoter, origin of replication and other control sequences is suitable to generate the components required to practice the method of the invention.

Plant cells including, but not limited to, crop plant cells, may be used as hosts to produce epitopes which are useful in the method of the invention. Control sequences compatible with plant cells such as the nopaline synthase promoter and polyadenylation signal sequences are known (see, e.g. Depicker et al., 1982, *J. Mol Appl. Gen* 1:561). In some preferred embodiments, the gene encoding the epitope is under the control of an ethylene responsive promoter such as, for example, the E8 promoter of tomatoes (Lincoln et al., 1988, *Mol. Gen. Genet.* 212:71–75; Deikman et al., 1988, *EMBO J.* 7:3315–3320). Thus, selective expression of an epitope may be achieved in this manner.

Insect cells may also be used as hosts to produce epitopes useful for the method of the invention, using methods and cells which are known in the art. To make such cells, a gene encoding the desired epitope is operably incorporated into insect cells using known methods (e.g., Griffiths et al., 1997, *Meth. Molec. Biol.* 75:427–440).

Depending on the type of host cell used, transformation is accomplished using standard techniques appropriate to such cells. The calcium treatment employing calcium chloride, as described by Cohen (1972, *Proc. Natl. Acad. Sci. USA* 69:2110), or methods described by Sambrook et al. (1989; *Molecular Cloning: A Laboratory Manual,* Cold Spring Harbor Laboratory, New York), may be used in the case of prokaryotes or other cells which contain substantial cell wall barriers. Infection with *Agrobacterium tumefaciens* (Shaw et al., 1983, *Gene* 23:315) is believed to be useful for certain plant cells. Transformation of DNA into yeast may be carried out according to the method of Van Solingen et al. (1977, *J. Bacteriol.* 130:946) and Hsiao et al. (1979, Proc. Natl. Acad. Sci. USA 76:3829). Genes may be transferred to plant cells using a variety of methods such as Agrobacterium plasmid-mediated gene transfer, (Truve et al., 1993, *Bio/Technology* 11: 1048; Streber et al., 1989, *Bio/Technology* 7:811; Mullins et al., 1991, *Bio/Technology* 8:1041; Mante et al., 1991, *Bio/Technology* 9:853; Dong et al., 1991, *Bio/Technology* 9:859; Penarrubia, 1992, *Bio/Technology* 10:561; D'Halluin, 1992, *Bio/Technology* 10:309) microparticle bombardment, (Vasil et al., 1991, *Bio/Technology* 9:743; Vasil et al., 1992, *Bio/Technology* 10:286)

electroporation, (Chupeau et al., 1989, *Bio/Technology* 7:503) liposome fusion, (Deshayes et al., 1985, *EMBO J.* 4:2731–2737) polyethylene glycol-mediated trasformation, (Potrykus et al., *Mol. Gen. Genet* 197:183–188) microinjection, (Griesbach, *Biotechnology* 3:348–350; Shewmaker, 1986, *Mol. Gen. Genet.* 202:179–185), viruses (Takematsu et al., *EMBO J.* 6:307–311), and geminivirus (Ward et al., 1988, *EMBO J.* 7:1583–1587).

cDNA or genomic libraries may be screened using the colony hybridization procedure. Generally, each microtiter plate is replicated onto duplicate nitrocellulose filter papers (e.g. S&S type BA-85) and colonies are allowed to grow at 37° C. for 14–16 hours on Luria broth agar containing 50 micrograms per milliliter ampicillin. The colonies are lysed and DNA is fixed to the filter by sequential treatment for five minutes with 500 millimolar NaOH, 1.5 molar NaCl, and the filter is washed twice for five minutes each time with 5×standard saline citrate (SSC). Filters are air dried and baked at 80° C. for two hours. Duplicate filters are prehybridized at 42° C. for 6–8 hours with ten milliliters per filter of a DNA hybridization buffer, such as one comprising 5×SSC adjusted to pH 7.0, 5×Denhardt's solution (0.02% (w/v) polyvinylpyrrolidone, 0.02% (w/v) Facial and 0.02% (w/v) bovine serum albumin), 50 mM sodium phosphate buffer adjusted pH 7.0, 0.02% (w/v) SDS, 20 micrograms per milliliter Poly U, and 50 micrograms per milliliter denatured salmon sperm DNA.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage can be performed by treating DNA with a suitable restriction enzyme(s) under conditions which are generally understood in the art, and the particulars of which are specified by the manufacturer of these commercially available restriction enzymes (see, e.g., New England Biolabs, Product Catalog). In general, about 1 microgram of plasmid or DNA sequence is cleaved by one unit of enzyme in about 20 microliters of buffer solution. Incubation times of about one hour to two hours at about 37° C. are workable, although variations can be tolerated. After each incubation, protein can be removed by extraction with phenol/chloroform, and may be followed by ether extraction, and the nucleic acid is recovered from aqueous fractions by precipitation with ethanol followed by chromatography using a Sephadex G-5 spin column. If desired, size separation of the cleaved fragments may be performed by polyacrylamide gel or agarose gel electrophoresis using standard techniques. A general description of size separations can be found in *Methods in Enzymology* (1980, 65:499–560).

Restriction-endonuclease-cleaved fragments may be blunt ended by treating with the large fragment of *E. coli* DNA polymerase I (Klenow) in the presence of the four deoxynucleotide triphosphates (dNTPs) using incubation times of about 15 to 25 minutes at from 20° C. to 25° C. in 50 millimolar Tris buffer at pH 7.6, 50 millimolar NaCl, 6 millimolar $MgCl_2$, 6 millimolar DTT and 5–10 micromolar dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by runing over a Sephadex G-50 spin column. Treatment under appropriate conditions with S1 nuclease results in hydrolysis of any single-stranded portion.

In some preferred embodiments of the present invention, expression of a viral coat protein such as a hepatitis B virus surface antigen, or a peptide comprising an epitope thereof, may be achieved in accordance with methods described by Valenzuela et al. (1982, *Nature* 298:347–350).

The invention also encompasses the use pharmaceutical compositions of an epitope which is useful in the method of the invention, the compositions comprising the epitope and a pharmaceutically acceptable carrier.

As used herein, the term "pharmaceutically acceptable carrier" means a chemical composition with which an epitope useful in the method of the invention may be combined and which, following the combination, can be used to administer the epitope to a mammal.

The pharmaceutical compositions useful for practicing the invention may be administered to deliver a dose of between 1 ng/kg/day and 100 mg/kg/day. In one embodiment, the invention envisions administration of a dose of the epitope comprising from about 0.1 milligram to about 250 milligrams per day to a human. In another embodiment, the human dose is from about 0.1 milligram to about 25 milligrams per day.

Pharmaceutical compositions that are useful in the methods of the invention may be administered systemically in oral solid formulations, ophthalmic, suppository, aerosol, topical, powdered, gel, or any other formulation known to be useful for transmucosal delivery of a pharmaceutically active agent. In addition to the epitope useful in the method of the invention, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer the epitope according to the methods of the invention.

The pharmaceutical composition useful in the method of the invention may further comprise any compound known to be effective for the treatment of infection of a mammal by an infectious agent or may further comprise any known immunosuppressive compound. The pharmaceutical composition may comprise, in addition to a molecule comprising an epitope described herein, a second molecule selected from the group consisting of an antibiotic, an antiviral compound, an antiparasitic compound, an anti-inflammatory compound, an immunosuppressant, and a synergist. An antibiotic is a composition which kills or inhibits the proliferation of a bacterium. An antiviral compound is a composition which inactivates or inhibits the proliferation of a virus. An antiparasitic compound is a composition which kills or inhibits the proliferation of a parasite. An anti-inflammatory compound is a composition which inhibits or alleviates inflammation in a mammal. An immunosuppressant is a composition which modulates an immune response in a mammal. A synergist is a composition which enhances induction of antigenic tolerance when administered to a mammal in combination with an epitope.

The pharmaceutical composition useful in the method of the invention may be administered to a mammal in a single dose, in multiple doses, in a continuous or sustained-release formulation, and the like.

Development of antigenic tolerance is dose-dependent over a broad range of dosages. However, it is generally the case that there are minimum and maximum effective dosages. As is understood by one skilled in the art, effective dosage for a patient suffering from a chronic infection may vary depending upon the form of the epitope. Moreover, the age, sex and physical condition of the patient, as well as other concurrent treatments being administered also have a bearing on the effective dosage. One skilled in the art would be able to adjust and refine the dosage used and the administration schedules to meet the individual needs of a patient.

Oral tolerance can be induced by employing small or large doses of epitopes. Generally low dosage regimes induce secretion of down regulatory cytokine mediators by regulatory cells. High dosage tolerance, commonly referred to as clonal anergy, employs a passive mechanism in which the clones of cells that are capable of responding to a given epitope are rendered non-responsive due to large concentrations of the epitope which are delivered across the mucosa. In some preferred embodiments of the present invention, low dosage regimes are preferred. Generally, administration to a human of an epitope in the form of about 0.1 mg to about 250 mg/day of peptide, protein, or glycoprotein will be effective in accordance some methods of the present invention. In other embodiments of the present invention, antigenic tolerance is achieved by administration to a human of amounts of peptide, protein or glycoprotein ranging from about 0.1 mg to about 25 mg/day.

Synergists may also be used in some embodiments of the present invention to enhance induction of antigenic tolerance. Synergists which have been found to enhance oral tolerance include bacterial lipopolysaccharides from a wide variety of gram negative bacteria such as various subtypes of *E. coli* and Salmonella (LPS and Lipid A, Sigma Chemical Co., St Louis, Mo.) and immunoregulatory lipoproteins, such as peptides covalently linked to tripalritoyl-S-glycarylcysteinyl-seryl-serine (prepared as described in Braun, 1976, *Biochim. Biophys. Acta* 435:335–337).

Examples of diseases which may be treated according to the methods of the invention are discussed herein. The invention should not be construed as being limited solely to these examples, as other autoimmune diseases which are caused or exacerbated by infection with an infectious agent and which are at present unknown, once known, are also treatable using the methods of the invention.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLE 1

A. Generation and Isolation of H2-restricted Cytotoxic Lymphocytes

MLE-10 cells, which were originally isolated as spontaneous immortalized transformants of normal mouse liver cells in culture (Lee et al., 1989, *Cancer Res.* 49:403–409), were co-transfected using two plasmids. The first plasmid contained a tandem head-to-tail dimer of the entire HBV genome which had previously been shown to be infectious in chimpanzees. The second plasmid contained the $neo^r$ gene, which confers neomycin resistance, for use as a selective marker in medium containing geneticin (G418). Transfected cells were plated in Weymouths 752/1 medium containing 10% (v/v) fetal calf serum, 50 micromolar streptomycin, 50 units per militer penicillin and 1 millimolar G418. After seventy-two hours incubation, surviving cells were collected and re-plated in the same medium at limiting dilution to allow for selection of colonies. Following an additional seventy-two hours incubation, randomly selected colonies were expanded. RNA was isolated from the selected colonies, and western blot analysis was performed to detect the presence of full length HBV transcripts. Several isolates found to be positive for the presence of such transcripts were tested for the presence of HBV in the culture supernatants using PCR analysis. Of the colonies which were determined to secrete virus, one was selected for expansion and the presence of cell-associated HBsAg or HBcAg was assessed by immunofluorescence. This cell line, herein designated MLE-10/HBV, was stained specifically with antisera specific for the two viral proteins.

MHC class I ($L^d$) inbred mice (Taconic Farms, Germantown, N.Y.)were immunized intraperitoneally with about $10^7$ syngeneic, viable MLE-10- or MLE-10/HBV-transfected cells. Each animal received a booster inoculation seven days later, and after another week selected animals were euthanized and the spleen of each was aseptically removed. Spleens were teased apart, and spleen cells were collected, counted, and seeded onto monolayers of either MLE-10 or MLE-10/HBV cells that had been exposed to 50 units per milliliter of recombinant gamma-interferon (Sigma Chemical Co., St. Louis, Mo.). The cells were left in place on the monolayer for from about eighteen to about twenty-four hours, after which time the cells were exposed to about 2000 rads of ionizing radiation. Spleen cells collected from MLE-10 immunized animals were seeded onto monolayers of MLE-10 stimulator cells, and spleen cells collected from MLE-10/HBV inoculated mice were transfed to monolayers of MLE-10/HBV cells. From five to seven days later, spleen cells were cultured in RPMI-1640 medium containing 10% (v/v) fetal calf serum, and 10% (v/v) conditioned medium collected from EL4.IL-2 murine lymphoma cells (American Type Culture Collection, Rockville Md.), which were induced with 20 nanograms per milliliter phorbal myristate acetate (Sigma Chemical Company, St. Louis, Mo.) and which were demonstrated to produce interleukin-2. Cytotoxic T lymphocytes (CTL) harvested from these mice are designated "$T_{HBimmune}$" herein.

Stimulated CTL were detected by collecting cultured spleen cells ("effector cells") and adding them, at varying effector-to-target cell ratios, to MLE-10 or MLE-10/HBV cells ("target cells") that had been loaded with $^{51}Cr$ using known methods. Briefly, target cells were detached from the culture substrate by treating them with trypsin. Detached target cells were washed, counted, and about $5 \times 10^5$ cells were transferred to 5 milliliter disposable culture tubes. The cells were pelleted, and the supernatant was removed. Aliquots comprising 20 microcuries of $^{51}Cr$ and a minimal volume were added to each tube, and the cells were incubated with periodic agitation for one hour at 37° C. The cells were washed twice, and about $10^4$ cells were added to each well of a 96 well cluster. Activated spleen cells were then added to each well at a concentrations sufficient to provide the ratio of effector-to-indicator cells indicated in Table 1, and the plates were incubated for four hours at 37° C. Aliquots comprising 100 microliters of the cell-free supernatant were collected, and the $^{51}Cr$ content of the supernatant was assessed. The $^{51}Cr$ content of aliquots of target cells lysed using 1% (w/v) SDS was also assessed, as was the $^{51}Cr$ content of samples collected from wells containing target cells alone (i.e. to quantify spontaneous release of the label). CTL activity was calculated by dividing the quantity determined by subtracting the degree of spontaneous $^{51}Cr$ release from the degree of experimental $^{51}Cr$ release by the quantity determined by subtracting the degree of spontaneous $^{51}Cr$ release from the total $^{51}Cr$ content of MLE-10/HBV target cells. Data from a typical experiment are presented in Table 1.

TABLE 1

Detection of stimulated CTL by detection of label release from cultured spleen cells. "γ-IFN" means gamma-interferon. "E:T" means the ration of effector cells to target cells.

| Effector cells were | | γ-IFN | Percent $^{51}$Cr released | | | |
|---|---|---|---|---|---|---|
| collected from mice immunized with: | Target cells | stim- ulated? | E:T 1:100 | E:T 1:33 | E:T 1:11 | E:T 1:4 |
| MLE-10/HBV | MLE-10 | no | 7 | 5 | 3 | 3 |
| MLE-10/HBV | MLE-10/ HBV | no | 13 | 10 | 9 | 7 |
| MLE-10/HBV | MLE-10 | yes | 7 | 6 | 6 | 2 |
| MLE-10/HBV | MLE-10/ HBV | yes | 25 | 23 | 19 | 15 |

Although the results obtained using this assay demonstrated that specific cytotoxic activity was present, it was present at levels significantly lower than those routinely reported by other researchers. In order to increase the number of CTLs present, a series of recombinant vaccinia virus constructs were developed, each comprising one of the four HBV genes. Two other constructs were developed, each comprising an open reading frame encoding an alternative translation product known to occur during HBV-infection of humans.

The plasmid (pTKHH-2) comprising the head-to-tail dimer of the HBV genome was digested using the restriction nucleases as described herein, and fragments were isolated by electrophoresis. The fragments were cloned into the shuttle vector pSC11 using the multiple cloning sites present in the construct, thereby generating the following series of plasmids, each comprising the following HBV genetic elements: pSC11-1PC, which comprised a 636 base pair region comprising the core gene accompanied by the pre-core region, pSC11-2C, which comprised a 549 base pair region comprising the core gene, pSC11-3PS, which comprised a 167 base pair region comprising both the pre-S and surface gene of the virus, pCS11-4S, which comprised a 678 base pair region comprising the surface gene of the virus, pCS11-5X, which comprised a 426 base pair region comprising the entire X-gene coding region, and pCS11-6P, which comprised a 2496 base pair region comprising the entire polymerase gene region.

These vaccinia virus constructs were expanded to produce viral stocks, the titer of each stock was determined using L929 cells, and the stocks were stored frozen until needed. A map of the genome of HBV and the open reading frames used in the constructions described herein is depicted herein in FIG. 1.

Mice were immunized by intraperitoneal administration of about $10^7$ plaque-forming units (PFU) of a single vaccinia virus construct Two weeks later, spleens were aseptically collected from immunized animals, and spleen cells were isolated. Contaminating red blood cells (RBC) were lysed using 0.4% (w/v) ammonium chloride, and the immune cells were stimulated in vitro by co-culture with MLE-10 or MLE-10/HBV cells in RPMI-1640 medium containing 10% (v/v) fetal calf serum, 10% (v/v) conditioned medium collected from EL4.IL-2 murine lymphoma cells (American Type Culture Collection, Rockville Md.). These latter cells were induced with 20 nanograms per milliliter phorbal myristate acetate (Sigma Chemical Company, St. Louis, Mo.) and produced interleukin-2. Following stimulation, immune cells were collected and processed as described herein in preparation for the CTL detection assay.

B. Generation and Isolation of H2 Restricted Suppressor Lymphocytes by Per Os Antigen Administration MHC class I ($L^d$) inbred mice are each fed one of two HBV antigens three times weekly for two weeks. Selected mice are fed HBsAg, and others are fed HBcAg. Suppressor T lymphocytes are harvested from the mice as described herein. For convenience, these HBV-tolerized suppressor T lymphocytes are refered to herein as $T_{HBtolerant}$.

Each antigen is suspended in phosphate buffered saline (PBS) at a concentration of 10 milligrams of an antigen per milliliter prior to feeding, and each mouse receives about one milligram per dose. The antigens are purified from an $E.$ $coli$ strain which is stably transfected using plasmid pTAC-10 which contains the coding region of the gene encoding HBcAg (Uy et al., 1986, Virology. 155:89–96). Transfected bacteria are inoculated into Luria broth comprising 50 micrograms per milliliter ampicillin and grown with constant agitation overnight. The culture is then diluted 1:10 with the broth, and IPTG is added to yield a final concentration of 0.2 millimolar. The culture is incubated until the optical density of the culture is in the range from about 1.0 to about 1.2, at which time the bacteria are pelleted by centrifligation and washed twice with PBS. For each gram of cells collected, 10 milligrams of lysozyme is mixed with a one milliliter suspension of the cells in PBS, and the mixture is incubated at room temperature for about thirty minutes. Nonspecific protease activity is inhibited by inclusion in the mixture of 10 microliters of a 0.2 molar solution of phenyl-methylsulfonylfluoride. Following incubation, the suspension is sonicated for a total of about sixty seconds using a sonicator (Heat Systems, Tarrytown, N.Y., model XL equipped with a microtip and adjusted to 30% magnitude). Following sonication, the suspension is centrifuged for about fifteen minutes in a benchtop microcentrifuge at about 35,000×g, and the supernatant is collected.

The supernatant is layered on top of a centrifuge tube containing a discontinuous step gradient of a CsCl solution which comprises layers having densities of 1.40, 1.35, 1.30, and 1.25 grams per milliliter. The tube is centrflged in an SW28 rotor for about sixty hours at 27,000 rotations per minute at 10° C., and fractions are collected. Fractions having a density between about 1.32 and about 1.38 grams per milliliter are pooled and dialyzed against PBS to remove CsCl. The pooled fractions are then concentrated approximately 10-fold and layered on top of a centrifuge tube containing a continuous CsCl gradient, wherein the density of the solution ranges from 1.05 to 1.30 grams per milliliter. This tube is centrifiged for about two hours at 34,000 rotations per minute in a Beckman SW41 rotor, and 0.5 milliliter fractions are collected. Fractions which are determined to contain immunoreactive HBcAg are pooled and dialyzed against PBS, and the purity of the antigen is determined by SDS-PAGE using Coomassie Brilliant Blue staining.

C. Suppression of Lysis of HBV Expressing Target Cells by T Lymphocytes from Orally Tolerized Mice Hepatocytes shown to express HBsAg, HBcAg, or both, are labeled with $^{51}$Cr by resuspending the cells in a minimal volume of culture medium and adding 100 microcuries of the isotope for about one hour. The cells are washed, resuspended in growth medium, and plated at a density which will allow approximately 75% confluence in repetitive wells of a multi-well tissue culture cluster. Following an approximately one hour period during which the hepatocytes ("target cells") attach to the wells, replicate wells are inoculated with either medium containing no added cells or medium containing $T_{HBimmune}$ ("effector") cells, as described herein, at concentrations which yield effector-to-target cell ratios of 1:5, 1:10, 1:20, and 1:50. Each well of another set of wells containing labeled hepatocytes is inoculated with medium containing $T_{HBtolerant}$ cells at the same ratios. A final set of wells containing labeled hepatocytes is inoculated with medium containing both $T_{HBimmune}$ and $T_{HBtolerant}$ cells mixed together at the effector-to-target cell ratios described herein. All wells are incubated for about sixteen hours in a 37° tissue culture incubator containing 5% (v/v) $CO_2$. Aliquots of culture supernatants from each well are quantitatively collected and transferred to gamma-counting tubes. The amount of radioactivity present in each sample is determined by detection of $^{51}Cr$ decay products.

The occurrence of cell death is manifested as a statistically significant increase in the amount of $^{51}Cr$ detected in the supernatant of individual wells containing both labeled hepatocytes and $T_{HBimmune}$ cells, relative to the amount detected in the supernatant of individual wells containing only labeled hepatocytes. Similarly, the ability of lymphocytes obtained from orally tolerized, syngeneic mice to suppress cell death induced by $T_{HBimmune}$ cells is manifested as a suppression of the amount of $^{51}Cr$ detected in the supernatant of individual wells containing labeled hepatocytes, $T_{HBimmune}$ cells, and $T_{HBtolerant}$ cells, relative to the amount detected in the supernatant of individual wells containing only labeled hepatocytes and $T_{HBimmune}$ cells. The inability of T cells isolated from allogeneic, HBV immunized animals to lyse labeled, HBV infected hepatocytes demonstrates that the cell death attributable to $T_{HBimmune}$ cells is induced in a CD-8 H-2 restricted fashion. CD-8 H-2 restricted cell death has been demonstrated by others to be pivotal in the pathogenesis of autoimmune diseases and in the pathogenicity of liver damage subsequent to chronic HBV infection.

The experiments described in this Example demonstrate that feeding an antigen derived from an infectious agent to a mouse results in production in the mouse of T lymphocytes which suppress cytotoxic T lymphocyte activity induced by the presence of the infectious agent in the mouse.

EXAMPLE 2

A. Generation of Genetically Immunodeficient Mice with Stably Integrated HBV that Express HBV Proteins Transgenic immunodeficient mice comprising a stably integrated copy of the HBV genome (SCID-HBV mice) were made by microinjection of the complete HBV genome into embryos of SCID mice.

The DNA injected into the mice was prepared as follows. DNA was excised, using the restriction endonuclease EcoRI, from the clone X"A", which is a head to tail dimer of HBV cloned into pBR322. This construct is known to infect HepG2 differentiated liver cells isolated from a human patient afflicted with hepatoblastoma. The restriction digest was electrophoresed through a Tris-acetate-EDTA gel and was collected from the medium by inserting a piece of DEAE paper immediately in front of the band of interest. The field power was then re-applied and the DNA was electrophoresed into and bound to the paper. The DEAE paper was removed from the gel and immersed in a minimal volume of a solution comprising 1 molar NaCl and 50 millimolar arginine (free base), and was incubated for approximately two hours at 65° C. to effect elution of DNA from the paper. Solubilized DNA was extracted using phenol/chloroform, and then chloroform, and was precipitated twice using ethanol and sodium acetate. Precipitated DNA was resuspended in injection buffer (which comprised 10 millimolar Tris buffer adjusted to pH 7.5 and 0.1 molar EDTA), and the DNA exaction and precipitation techniques were repeated. The resulting DNA was solubilized in injection buffer and quantified prior to injection into mouse embryos.

CB.17 SCID female mice (Taconic Farns, Germantown, N.Y.) were injected with 5 IU of human chorionic gonadotropin in pregnant mare serum to induce superovulation. Following the serum/gonadotropin injection, the mice were mated with syngeneic stud males, and embryos were obtained on about day 0.5 of pregnancy. The embryos were flushed from the fallopian tubes into Whittens 640 medium which contained hyaluronidase to detach adherent follicle cells. Following incubation at 37° C. for about sixty minutes, the embryos were microscopically examined for normal morphology, and aberrant embryos were removed. Normal appearing embryos were placed in a drop of Whittens 640 medium, and were transferred to an inverted microscope equipped with micromanipulators. Individual embryos were gently affixed to a microbore suction pipet, and oriented with the male pronucleus distal to the attachment point. The DNA solution described herein was then injected into the male pronucleus. Each embryo received from about one 1 to about 2 microliters of the solution. After washing each embryo with medium, the injected embryos were maintained overnight at 37° C. in Whittens 640 mediumin an atmosphere comprising 5% (v/v) $CO_2$, 5% (v/v) $O_2$, 90% (v/v) nitrogen.

CB.17 SCID female mice were copulated with vasectomized syngeneic males to induce a state of pseudopregnancy. These mice were anesthetized with Avertin (2% w/v in sterile saline) and the fallopian tubes and ovaries were aseptically resected. The embryos described herein were trasferred to the exposed ampulla, and the incisions were closed using a wound clip. Animals were allowed to recover on a 37° C. warming tray, and were then housed singly or in pairs until litters were born.

Mouse pups were tested for the presence of the transgene by isolating DNA from samples of tail tissue. Tissue was digested by incubating it overnight in a solution comprising 20 milliliters of proteinase K (17.8 micrograms per milliliter) at 55° C. DNA was extracted from the tissue using a QIA Amp™ tissue kit (QIAGEN, Hilden, Germany) by adding 410 microliters of the buffer Al/ethanol mixture which was supplied in the kit, and application to a QIA Amp™ column. The column was centrifuged for 1 minute at 6000×g, and was then washed twice with the AW buffer which was supplied in the kit. Isolated DNA was collected by washing the column with 200 microliters of distilled water, and was amplified by PCR. The PCR reaction mixture comprised 40 microliters of isolated mouse DNA suspension, which comprised about 1 microgram of DNA, as a template, 10 millimolar Tris buffer adjusted to pH 8.3 using HCl, 50 millimolar KCl, 1.5 millimolar $MgCl_2$, 0.1% (w/v) gelatin, 0.2 millimolar of each of the four deoxynucleotides (Pharmacia, Lt. Milton Keynes, UK), 0.2 millimolar primer MFO3 (having the nucleotide sequence 5'-ATGGACATCGACCCTTATAAAGAATTTG-3'; SEQ ID NO: 1), 0.2 millimolar primer MFO4 (having the nucleotide sequence 5'-CTAAGGATTGAGATCTTCTGCGACGCGG-3'; SEQ ID NO: 2), and 2.5 units of TAQ polymerase (Perkin Elmer, Norwalk Conn.) in a 120 microliter reaction mixture. Following an initial denaturation of the DNA at 99° C. for five minutes, and at 94° C. for one minute, primer annealing was performed at 55° C. for one minute and extension at 72° C. for one minute. The 94° C.–55° C.–72° C. cycle was repeated for atotal of 35 cycles. Control samples included all reagents, except that water was substituted in place of mouse DNA. Amplified products were electrophoretically resolved in a 1.4% (w/v) agarose gel, and bands of the expected molecular weight were identified following ethidium bromide staining.

HBV was detected by layering serum samples obtained from the mice on top of a centrifige tube containing a continuous CsCl gradient prepared from CsCl solutions having densities of 1.19 and 1.40 grams per mililiter. Using a gradient maker, a 4.5 milliliter gradient was prepared in 13×51 millimeter Beckman Ultraclear™ ultracentrige tube, and an individual serum sample was layered on top of the tube. Each tube was centged for about 66.5 hours at 45,000 revolutions per minute in an SW47 rotor, after which approximately 0.3 milliliter fractions were collected. The density of each faction was determined by assessing the refractive index of the fraction, and the presence of virus in sample fractions having a density between 1.22 and 1.33 was determined by PCR as described. Oligonucleotide bands corresponding to the expected molecular weights characteristic of HBV were detected in fractions, suggesting that intact virus is present in the blood of the transgenic animals.

Following identification of founder animals that express the viral proteins, the animals are bred with H-2L$^d$ mice to provide C3H/6H-2L$^d$ F1 crosses, which are backcrossed for a minimum of 6 generations to establish a line of H-2L$^d$ mice which express HBV proteins.

Syngeneic immunocompetent donor mice were euthanized and their spleens were aseptically collected. The organs were teased apart, and a single-cell suspension was collected. The cells were washed twice in PBS and resuspended in sterile PBS at a density of about 5×10$^7$ cells per milliliter.

Randomly selected immunodeficient HBV transgenic mice were assigned to test groups designated to receive an infusion of competent immune cells or an equivalent volume of PBS. Another group of mice comprised littermates of the HBV transgenic immunodeficient mice which tested negative for the presence of the transgene by PCR. These mice were likewise randomly assigned to test groups, and also received infusions of immunocompetent immune cells or PBS. Transgenic and nontransgenic SCID mice which received an infusion of immune cells had 'reconstituted' immune systems. Injections in all mice were made in either the right or the left tail vein.

Figure 2:
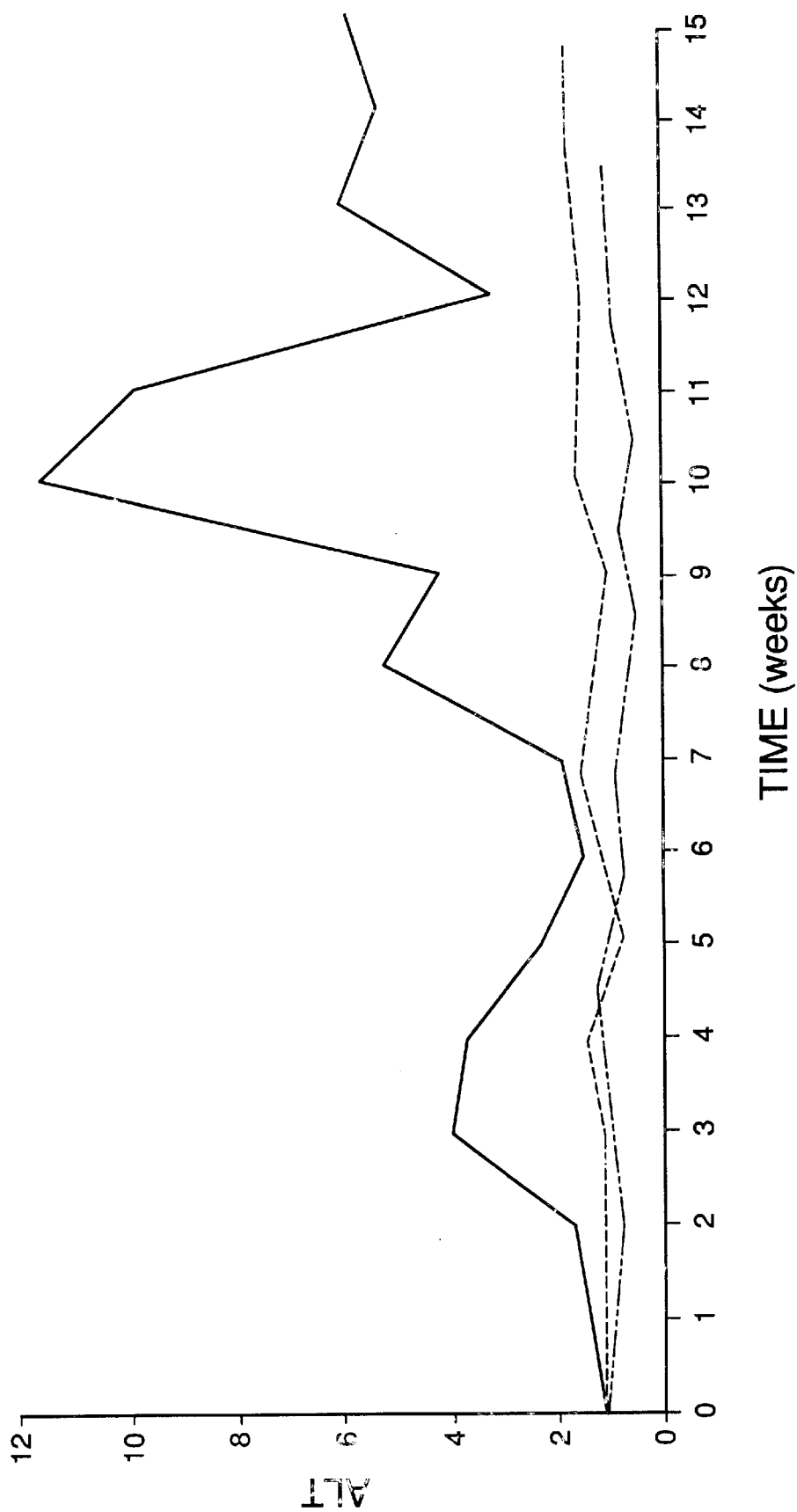
FIG. 2 is a graph which depicts the amount of alanine amino transferase (ALT; represented by the vertical axis) detected in the circulation of SCID-HBV mice, as assessed at selected times following injection of the mice with a solution which consisted of either physiological saline solution or splenic cells derived from immunocompetent mice suspended in physiological saline solution. The solid line represents the amount of ALT detected in the serum of individual SCID-HBV mice which were injected with splenic cells derived from immunocompetent mice. The dashed line represents the amount of ALT detected in the serum of individual SCID HBV mice which were injected with physiological saline solution. The line comprising dashes and dots represents the amount of ALT detected in the serum of individual SCID mice which did not comprise the HBV genome and which were injected with splenic cells derived from immunocompetent mice.

Randomly selected animals in each group were euthanized periodically over the ensuing eight weeks. Blood samples collected from individual animals were tested for the amount of alanine amnio transferase (ALT) present in the sample. ALT is an enzyme which has been determined to be present in the greatest amounts in hepatocytes and serves as a specific biochemical marker of hepatocyte damage. Animals were tested after eight weeks by collecting blood samples from retro-orbital bleeds. The graph depicted in FIG. 2 indicates that all HBV transgenic immunodeficient mice that received immune reconstitution developed elevated ALT levels in their sera st at eleven weeks post injection. ALT concentration was determined using a commercial kit supplied by Sigma Chemical Co. (St Louis, Mo.). No analogous elevated ALT concentration was detected in the samples collected from non-transgenic animals. Thus, these results indicate that a prolonged hepatocellular necrosis occurred in the mice having reconstituted immune systems.

Figures 3A, 3B, 3C:
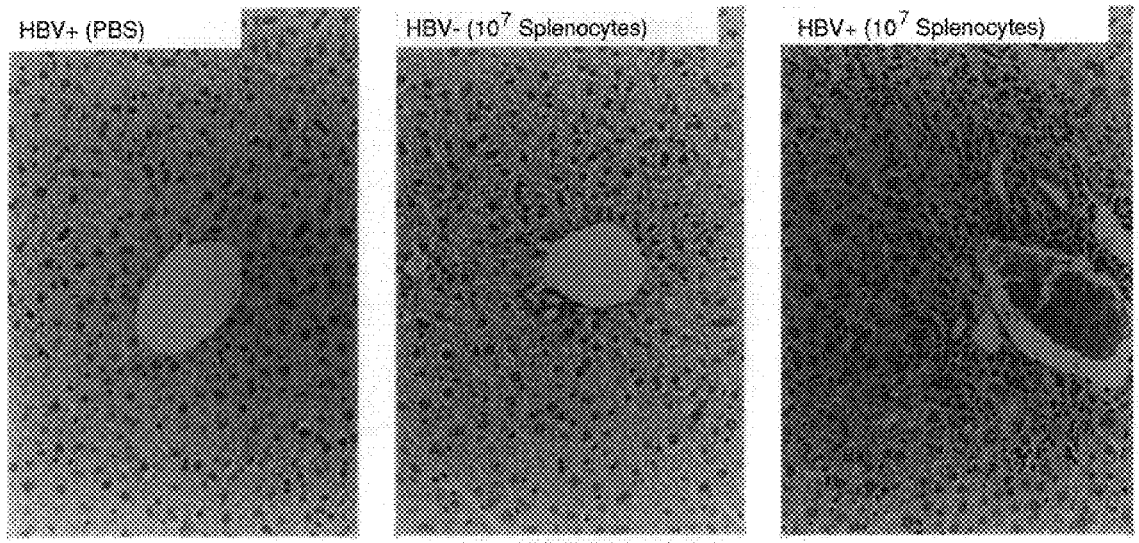
FIG. 3, comprising Panels A, B, and C, is a trio of images which depict stained hepatic tissue sections obtained from mice. The section in Panel A depicts stained hepatic tissue obtained from a severe combined immunodeficient transgenic mouse comprising a copy of the hepatitis B virus genome (i.e. a SCID-HBV mouse). The section in Panel B depicts stained hepatic tissue obtained from a SCID mouse which did not comprise the HBV genome, which was a littermate of a SCID-HBV mouse, and which was injected with splenic cells obtained from an immunocompetent mouse. The section in Panel C depicts stained hepatic tissue obtained from a SCID-HBV mouse which was injected with splenic cells obtained from an immunocompetent mouse.
Figures 4A, 4B, 4C:
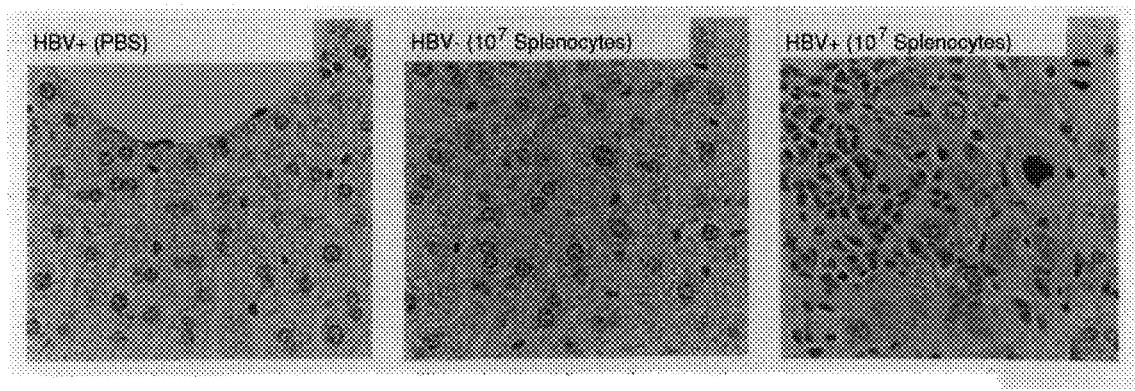
FIG. 4, comprising Panels A, B, and C, is a trio of images which depict stained hepatic tissue sections obtained from mice. The section in Panel A depicts stained hepatic tissue obtained from a SCID-HBV mouse. The section in Panel B depicts stained hepatic tissue obtained from a SCID mouse which did not comprise the HBV genome, which was a littermate of a SCID-HBV mouse, and which was injected with splenic cells obtained from an immunocompetent mouse. The section in Panel C depicts stained hepatic tissue obtained from a SCID-HBV mouse which was injected with splenic cells obtained from an immunocompetent mouse.
Figures 5A, 5B, 5C:
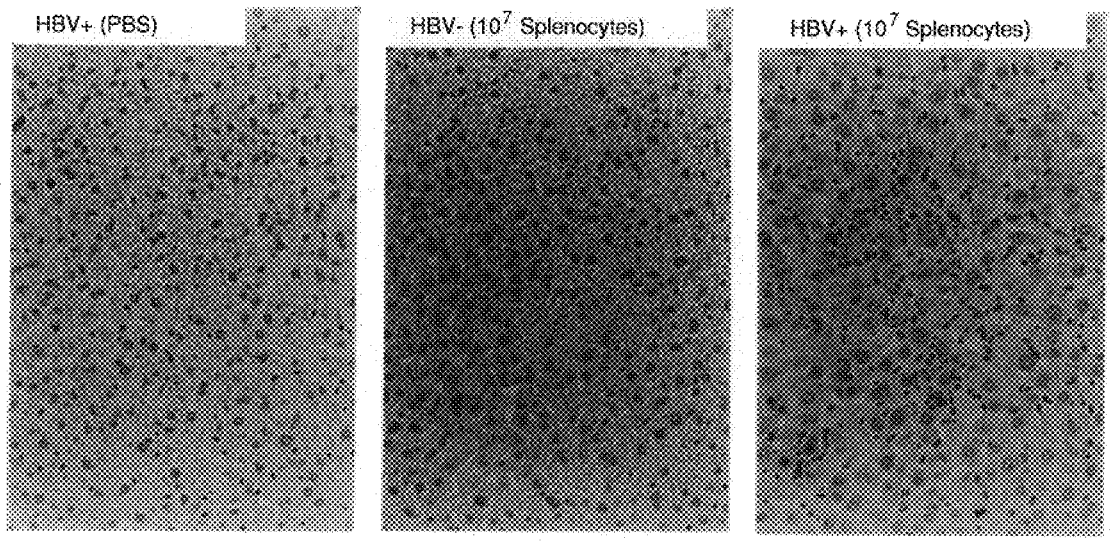
FIG. 5, comprising Panels A, B, and C, is a trio of images which depict stained hepatic tissue sections obtained from mice. The section in Panel A depicts stained hepatic tissue obtained from a SCID-HBV mouse. The section in Panel B depicts stained hepatic tissue obtained from a SCID mouse which did not comprise the HBV genome, which was a littermate of a SCID-HBV mouse, and which was injected with splenic cells obtained from an immunocompetent mouse. The section in Panel C depicts stained hepatic tissue obtained from a SCID-HBV mouse which was injected with splenic cells obtained from an immunocompetent mouse.

Liver samples were collected from the mice and were processed for immunohistochemistry after fixation in buffered formalin. Following staining with hematoxylin and eosin, infiltrating immune cells could be visualized, especially in periportal areas again indicating that a hepatocellular necrosis identical to that observed in humans with HBV mediated liver disease was occurring. Images of stained liver samples are presented in FIGS. 3 through 5.

B. Generation and Isolation of H2 Restricted Cytotoxic Lymphocytes

H2 restricted cytotoxic lymphocytes were prepared as described herein in Example 1. CTL were detected using the CTL detection assay described herein in Example 1.

C. Generation and Isolation Of H2 Restricted Suppressor Lymphocytes by Per Os Antigen Administration H2 restricted suppressor T lymphocytes were prepared as described herein in Example 1.

D. Suppression of Hepatocellular Destruction in Severe Combined Immunodeficient Mice Transgenic for HBV (SCID-HBV Mice) Effected by Administration of T Lymphocytes Obtained from Orally Tolerized Syngeneic Mice SCID-HBV mice exhibited no liver disease over 5 generations of the animals. SCID-HBV mice experienced HBV protein-mediated lived disease following immune reconstitution, as indicated by the appearance of inflammatory cell infiltration in the livers of such mice, which is depicted in Panel C of each of FIGS. 3 through 5. In additional, the prolonged, statistically significantly elevated levels of ALT detected in the circulation of these mice, but not in the circulation of control mice clearly indicates the onset of liver disease.

Hepatocyte lysis was induced by collecting $T_{HBimmune}$ cells from the spleens of immunocompetent syngeneic animals, as described herein, and injecting between about 10$^5$ and 10$^7$ viable $T_{HBimmune}$ cells either intraperitoneally or intravenously into SCID-HBV mice. Blood samples were collected from mice so injected every twenty-four hours post-injection, and the concentration of the liver-specific marker enzyme ALT was determined as described herein. After ninety-six hours, the mice were euthanized, and the livers were perfused with PBS and 30% formalin to fix tissues. The tissues were embedded in paraffin and 5-micrometer-thick histopathological sections prepared using a microtome. The sections were evaluated by a blinded observer to quantify the number of infiltrating inflammatory cells in hepatic tissue sections. Control animals included SCID-HBV mice which received injections of a volume of saline equal to tha used to suspend the transferred immune lymphocytes and littermates of the SCID-HBV mice which did not comprise a copy of the HBV genome and which received injections of lymphocytes derived from immunocompetent mice.

To demonstrate that $T_{HBtolerant}$ cells can block liver destruction mediated by $T_{HBimmune}$ cells, injection of both types of cells into SCID-HBV mice was performed. SCID-HBV mice received between about 10$^5$ and about 10$^7$ viable $T_{HBimmune}$ cells by either intraperitoneal or intravenous injection. Selected SCID-HBV mice simultaneously received between about 10$^5$ and about 10$^7$ $T_{HBtolerant}$ cells collected from orally tolerized mice, as described herein. Blood samples were collected from the mice every twenty-four hours following transfer of the cells, and the concentration of the liver-specific marker enzyme ALT in those samples was detemined for the next four days. After ninety-six hours, the mice were euthanized, and their livers were perfused with PBS and 30% (v/v) formalin to fix tissues. The tissues were embedded in paraffin and 5 micrometer-thick histopathological sections were prepared using a microtome. The sections were evaluated by a blinded observer to quantify infiltrating inflammatory cells in hepatic tissue samples. Control ammals included SCID-HBV mice which received injections of a volume of saline equal to that used to suspend the transferred immune lymphocytes and littermates of the SCID-HBV mice which did not comprise a copy of the HBV genome and which received injections of lymphocytes derived from immunocompetent mice.

EXAMPLE 3

Expression of HBV Proteins In Transgenic Plant Cells

A tobacco mosaic virus (TMV) expression vector (Biosource Genetics, Inc., Vacaville, Calif.) designed for the expression of transgenic proteins in intact plants and plant cells is selected. The entire coding sequence of the gene encoding HBcAg which is contained in plasmid pTACC10 is excised using PvuII and BamHI restriction endonuclease digestion, isolated, and purified as described (Uy et al., 1986, *Virology* 155:89–96). The resulting fragments are cloned into plasmid pBGC150 using multiple cloning sites as described to yield an operable vector (Kamagi et al., 1993, *Proc. Natl. Acad. Sci. USA* 90:427–430). Orientation of the insert is verified by analysis of PCR products.

In vitro transcripts of the operable vector are made following digestion of the vector using the restriction endonuclease KpnI, and 50 micrograms of the resulting RNA is transfected into about $5 \times 10^6$ BY2 cells (American Type Culture Collection, Rockville, Md.) by electroporation using the conditions similar to those found optimal by Matsunaga et al. (1992, *J. Gen. Virol.* 73:763–766). Following electroporation, cells are incubated for from about twenty-four to about forty-eight hours. Whole cell extracts are then made by freezing and thawing the cells, using a known procedure. Western Blot analysis is used to confirm that the transgenic protein is immunologically reactive with anti-HBV-core antiserum. About 50 micrograms of the RNA is transfected into from about six- to about eight-week-old tobacco seedlings using the methods of Kamagi et al (1993, *Proc. Natl. Acad. Sci. USA* 90:427–430). Leaf samples distal to the inoculation site are sampled about every four or five days, and viral protein expression is detected by Western blot analysis. Quantitation of protein expression is performed using an ELISA kit (e.g. the Corzyme™ kit, Abbot Laboratories, Abbott Park, Ill.).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of modulating an immune response in a mammal infected with an infectious agent, said method comprising transmucosally administering a composition to said mammal, said composition comprising an epitope which is located in close proximity to said immune response, wherein said modulation comprises induction of oral tolerization to said antigen.

2. The method of claim 1, wherein said mammal is chronically infected with said infectious agent.

3. The method of claim 1, wherein said infectious agent comprises an antigen which comprises said epitope.

4. The method of claim 3, wherein said composition comprises said antigen.

5. The method of claim 1, wherein said epitope is located on a tissue antigen of the mammal.

6. The method of claim 5, wherein said antigen reacts with a component of the immune system of said mammal only when said mammal is infected with said infectious agent.

7. The method of claim 6, wherein said component is selected from the group consisting of an antibody molecule, a complement molecule, a B lymphocyte, a T lymphocyte, a helper T lymphocyte, a suppressor T lymphocyte, a cytotoxic T lymphocyte, an immunosuppressive lymphocyte, a cytoline-secreting lymphocyte, a non-cytotoxic lymphocyte, a macrophage, a neutrophil, a mast cell, a basophil, an eosinophil, and a monocyte.

8. The method of claim 1, wherein said mammal is a human.

9. The method of claim 1, wherein said composition further comprises a second molecule selected from the group consisting of an antibiotic, an antiviral compound, an antiparasitic compound, an anti-inflammatory compoumd, an immumosuppressant, and a synergist.

10. The method of claim 9, wherein said second molecule is selected from the group consisting of lamivudine, a bacterial lipopolysaccharide, an immunoregulatory lipoprotein, a peptide covalently linked to tripalmitoyl-S-glycarylcysteinyl-seryl-serine, a steroid, cyclosporin A, AZT, ddC, ddI, and 3TC.

11. The method of claim 1, wherein said infectious agent is selected from the group consisting of a bacterium, a virus, and a parasite.

12. The method of claim 11, wherein said infectious agent is selected from the group consisting of hepatitis B virus, hepatitis C virus, parvovirus B19, Borna disease virus, HIV, HTLV-1, *Mycobacterium tuberculosis*, a group B hemolytic *Streptococcus bacterium, S. mutans, Trypanosoma cruzi, Leishmania donovani, Onchocerca volvulus, T. braziliensis,* and *S. mansoni.*

13. The method of claim 12, wherein said infectious agent is hepatitis B virus.

14. The method of claim 12, wherein said infectious agent is hepatitis C virus.

15. The method of claim 1, wherein said immune response is selected from the group consisting of an autoimmune reaction, a humoral immune response, and a cellular immune response.

16. The method of claim 15, wherein said autoimmune reaction is selected from the group consisting of a humoral immune response comprising production of an antibody which cross-reacts with a tissue antigen of said mammal, a humoral immune response comprising production of an immunosuppressive factor, a cellular immune response comprising production of a cytotoxic cell which specifically induces cell death in a tissue of said mamnal, and a cellular immune response comprising production of a lymphocyte which secretes an immunosuppressive factor.

17. The method of claim 1, wherein said transmucosal administration of said composition is accomplished by a route of administration selected from the group consisting of oral, enteral, intranasal, pulmonary, and colonic.

18. The method of claim 1, further comprising administering to said mammal a composition comprising a second molecule selected from the group consisting of an antibiotic, an antiviral compound, an antiparasitic compound, an anti-inflammatory compound, an immunosuppressant, and a synergist.

19. The method of claim 18, wherein said second molecule is selected from the group consisting of lamivudine, a bacterial lipopolysaccharide, an immunoregulatory lipoprotein, a peptide covalently linked to tripaimitoyl-S-glycarylcysteinyl-seryl-serine, a steroid, cyclosporin A, AZT, ddC, ddI, and 3TC.

20. A method of modulating an immune response in a mammal infected with an infectious agent, said method comprising transmucosally administering a composition to said mammal, said composition comprising an epitope which is located in close proximity to said immune response, wherein the modulation comprises an induction of an immune hyporesponsiveness to the epitope.

21. The method of claim 20, wherein said epitope is located on a tissue antigen of the mammal.

22. The method of claim 21, wherein the antigen reacts with a component of the immune system of the mammal only when the mammal is infected with the infectious agent.

23. The method of claim 20, wherein the mammal is a human.

24. The method of claim 20, wherein the composition further comprises a second molecule selected from the group consisting of an antibiotic, an antiviral compound, an anti-parasitic compound, an anti-inflammatory compound, and immunosuppressant, and a synergist.

25. The method of claim 24, wherein the second molecule is lamivudine.

26. The method of claim 20, wherein the infectious agent is selected from the group consisting of a bacterium, a virus, and a parasite.

27. The method of claim 26, wherein the infectious agent is hepatitis B virus.

* * * * *

UNITED STATES PATENT AND TRADEMARK OFFICE
CERTIFICATE OF CORRECTION

PATENT NO. : 6,355,248 B1
DATED : March 12, 2001
INVENTOR(S) : Frank Michaels and Timothy Block It is certified that error appears in the above-identified patent and that said Letters Patent is hereby corrected as shown below:

<u>Column 1,</u>
Line 9, change "publication no. WO 98/29121)" to -- (publication no. WO 98/29121) --

<u>Column 5,</u>
Line 12, change "Sleeping. Sickness" to -- Sleeping Sickness --

<u>Column 10,</u>
Line 21, insert -- of -- between "more" and "these"
Line 25, change "no," to -- not, --

<u>Column 11,</u>
Line 56, change "designnted" to -- designated --.
Line 66, delete the period after "tissue"

<u>Column 13,</u>
Line 20, insert -- of -- between "method" and "the"
Line 36, change "transfrrned" to -- transferred --

<u>Column 18,</u>
Line 29, change "transfed" to -- transferred --

<u>Column 19,</u>
Line 54, insert a period after "construct"

<u>Column 20,</u>
Line 39, change "contrflged" to -- centrifuged --

<u>Column 22,</u>
Line 65, change "atotal" to -- a total --

<u>Column 23,</u>
Line 5, change "centrifige" to -- centrifuge --
Line 11, change "contged" to -- centrifuged --
Line 14, change "faction" to -- fraction --
Line 56, change "st" to -- starting --

UNITED STATES PATENT AND TRADEMARK OFFICE
CERTIFICATE OF CORRECTION

PATENT NO.   : 6,355,248 B1
DATED        : March 12, 2001
INVENTOR(S)  : Frank Michaels and Timothy Block It is certified that error appears in the above-identified patent and that said Letters Patent is hereby corrected as shown below:

<u>Column 24,</u>
Line 44, change "tha" to -- that --

Signed and Sealed this

Third Day of December, 2002

JAMES E. ROGAN
*Director of the United States Patent and Trademark Office*